(12) United States Patent
Bhullar et al.

(10) Patent No.: US 6,319,719 B1
(45) Date of Patent: Nov. 20, 2001

(54) CAPILLARY HEMATOCRIT SEPARATION STRUCTURE AND METHOD

(75) Inventors: Raghbir S. Bhullar, Indianapolis; Christopher D. Wilsey, Carmel; Jeffrey N. Shelton, Fishers, all of IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/428,691

(22) Filed: Oct. 28, 1999

(51) Int. Cl.[7] .......................... G01N 33/86; G01N 33/48; G01N 21/11
(52) U.S. Cl. .................... 436/70; 436/165; 436/175; 436/177; 422/58; 422/73; 422/101; 422/102
(58) Field of Search ................ 436/70, 164, 165, 436/175, 177; 422/55, 58, 73, 101, 102

(56) References Cited

U.S. PATENT DOCUMENTS

| | | |
|---|---|---|
| 4,233,029 | 11/1980 | Columbus . |
| 4,271,119 | 6/1981 | Columbus .......................... 422/50 |
| 4,302,313 | 11/1981 | Columbus . |
| 4,310,399 | 1/1982 | Columbus . |
| 4,426,451 | 1/1984 | Columbus .......................... 436/518 |
| 4,439,526 | 3/1984 | Columbus .......................... 436/180 |
| 4,473,457 | 9/1984 | Columbus . |
| 4,549,952 | 10/1985 | Columbus . |
| 4,618,476 | 10/1986 | Columbus .......................... 422/100 |
| 4,753,776 | 6/1988 | Hillman et al. .................... 422/101 |
| 4,756,884 | 7/1988 | Hillman et al. .................... 422/73 |
| 4,849,340 | 7/1989 | Oberhardt .......................... 435/13 |
| 4,948,961 | 8/1990 | Hillman et al. . |
| 4,957,582 | 9/1990 | Columbus . |
| 4,963,498 | 10/1990 | Hillman et al. .................... 436/69 |
| 4,983,038 | * 1/1991 | Ohki et al. .......................... 356/246 |
| 5,004,923 | 4/1991 | Hillman et al. . |
| 5,039,617 | 8/1991 | McDonald et al. .................... 436/69 |
| 5,051,237 | * 9/1991 | Grenner et al. .................... 422/56 |
| 5,135,716 | 8/1992 | Thakore .......................... 422/56 |
| 5,135,719 | 8/1992 | Hillman et al. .................... 422/101 |
| 5,140,161 | 8/1992 | Hillman et al. . |
| 5,144,139 | 9/1992 | Hillman et al. . |

(List continued on next page.)

FOREIGN PATENT DOCUMENTS

| | | |
|---|---|---|
| 0 289 269 A2 | 11/1988 | (EP) . |
| 0 388 782 A1 | 9/1990 | (EP) . |
| 0 408 222 A1 | 1/1991 | (EP) . |
| 0 408 223 A1 | 1/1991 | (EP) . |
| WO 99/30158 | 6/1999 | (WO) . |
| WO 00/60352 | 10/2000 | (WO) . |

Primary Examiner—Maureen M. Wallenhorst
(74) Attorney, Agent, or Firm—Brinks Hofer Gilson & Lione

(57) ABSTRACT

A capillary hematocrit separation structure is included within a housing having a fluid inlet port, a reaction region, and a capillary pathway connecting the inlet port and the reaction region. The capillary pathway is dimensioned so that the driving force for the movement of liquid through the capillary pathway arises from capillary pressure. A plurality of obstructions are fixed in the capillary pathway, each obstruction having a concave portion facing toward the vented reaction region on the down stream side of the obstructions as viewed with reference to a liquid flowing from the inlet port to the reaction region. The capillary pathway in a hematocrit separation structure for a single drop sample size includes about $10^5$ obstructions, each obstruction including a concave portion having a volume of between about $10^{-4}$ to $10^{-5}$ $\mu l$ for selectively receiving hematocrit.

27 Claims, 5 Drawing Sheets

U.S. PATENT DOCUMENTS

| | | |
|---|---|---|
| 5,164,598 | 11/1992 | Hillman et al. . |
| 5,204,525 | 4/1993 | Hillman et al. . |
| 5,208,147 * | 5/1993 | Kagenow et al. ............ 435/14 |
| 5,230,866 | 7/1993 | Shartle et al. ............ 422/103 |
| 5,300,779 | 4/1994 | Hillman et al. . |
| 5,418,142 | 5/1995 | Kiser et al. ............ 435/14 |
| 5,540,888 | 7/1996 | Bunce et al. ............ 422/100 |
| 5,620,863 | 4/1997 | Tomasco et al. ............ 435/14 |
| 5,658,444 | 8/1997 | Black et al. . |
| 5,798,031 | 8/1998 | Charlton et al. . |
| 5,885,527 | 3/1999 | Buechler ............ 422/58 |
| 5,976,336 | 11/1999 | Dubrow et al. . |
| 6,113,855 * | 9/2000 | Buechler ............ 422/58 |
| 6,156,270 * | 12/2000 | Buechler ............ 422/58 |

* cited by examiner

CAPILLARY HEMATOCRIT SEPARATION STRUCTURE AND METHOD

BACKGROUND OF THE INVENTION

The present invention is directed to physical structures and methods for separating hematocrit out of small volume whole blood samples leaving merely the plasma or plasma containing a substantially reduced partial volume of hematocrit. The present invention is particularly directed to such structures having no moving parts which subsequent to separation of the plasma would facilitate contacting the reduced hematocrit content plasma with a dry reagent to permit an accurate detection of an analyte.

Many diagnostic tests are carried out in the clinical field utilizing a blood sample. It is desirable, when possible, to use a very small volumes of blood, often no more than a drop or two. Capillary structures are often employed when handling such small volumes of blood or other fluids. The presence of the hematocrit in the blood sample often interferes with accurate testing and so the removal of, or reduction in concentration of, the hematocrit in the sample, leaving a reduced hematocrit content plasma for testing, is often desirable or even necessary. The removal of the hematocrit is often done using a filter. An example of such a filter device employing capillary structures is described in Hillman, et al., U.S. Pat. Nos. 4,753,776 and 5,135,719. Other devices employing capillary structures to handle whole blood samples are disclosed in McDonald, et al., U.S. Pat. No. 5,039,617; Hillman, et al., U.S. Pat. No. 4,963,498; and Columbus, U.S. Pat. No. 4,271,119.

While such filter devices generally perform satisfactorily, many filter materials tend to absorb a significant portion of the plasma from the blood sample thus leaving only a small volume of the reduced plasma for analytical testing. As the total volume of the sample is diminished, the proportion of the plasma fraction that is absorbed by the filter tends to increase leaving even smaller volumes for testing. It is therefore desirable to construct alternative means for removing hematocrit from whole blood that would be usable on very small sample volumes.

SUMMARY OF THE INVENTION

A capillary hematocrit separation structure according to the present invention is included within a housing having a fluid inlet port, a vented reaction region, and a capillary pathway connecting the inlet port and the reaction region. The capillary pathway is dimensioned so that the driving force for the movement of liquid through the capillary pathway arises from capillary pressure. A plurality of obstructions are fixed in the capillary pathway, each obstruction having a concave portion facing toward the vented reaction region. The situation of the concave portion is to be understood, in reference to the flow of liquid from the fluid inlet port to the reaction region, to be positioned on the down stream side of the obstructions.

The obstructions can take on a variety of shapes including a bullet shape and a quarter moon shape, a ¾ quarter moon shape being preferred. The obstructions are to be situated far enough from each other so that their mere proximity to each other does not create a filter effect, yet they are to be situated close enough to each other as to minimize the volume of liquid retained in the capillary pathway. Preferably, the obstructions are separated from each other, on a nearest neighbor basis, by about $10^{-5}$ meters, and arranged in a hexagonal close-pack configuration.

The number of obstructions to be employed is determined by the capacity of the concave portions of the obstructions. It has been observed that as whole blood flows through a capillary pathway containing a plurality of obstructions in accordance with the present invention, hematocrit collects in the concave portions of the obstructions. While it was initially thought that the hematocrit collected by virtue of Von Karmen vortices, it has now been determined that such vortices only occur in turbulent flow circumstances, and the passage of blood through a capillary channel is probably laminar. The mechanism behind this effect has not been identified, but the effect is significant enough to permit substantial reduction in the partial volume of hematocrit in whole blood samples.

It is desirable that sufficient obstructions are employed to provide concave portions having a total volume exceeding the volume of hematocrit in the expected sample size. In a preferred embodiment the volume of each concave portion is about $10^{-13}$ to $10^{-14}$ m$^3$, or $10^{-4}$ to $10^{-5}$ μl. A sample comprising a single drop of blood typically has a volume of 20 to 50 μl., of which typically 35% to 45% constitutes hematocrit. Even smaller volumes of whole blood are often used by diabetics and others during testing, the smaller volume being achieved by expressing the blood sample from a small cut or puncture, in which case the volume of the sample may amount to only 2 to 10 μl. A capillary hematocrit separation structure according to the present invention capable of separating the hematocrit from a single drop sample size includes about $10^4$ to $10^5$ obstructions. A capillary pathway in such a structure can be a rectangular channel about 100 μm high or less, 2 to 5 mm wide, and up to 70 mm long. The volume of the inlet port leading to the capillary pathway is generally less than about 50 μl, and preferably the sum of the inlet port volume and the capillary pathway volume is less than about 20 μl.

It is to be understood that the number of capillary pathways between the fluid inlet port and the reaction region is not critical and that one or more than one can be employed, if desirable, to facilitate to the construction of the obstructions or other features of the device. While the hematocrit is observed to preferentially accumulate in the concave portions, it is also observed to accumulate to a lesser extent in other regions of the structure, particularly adjacent to the walls defining the capillary pathway.

A capillary hematocrit separation structure according to the present invention can be molded as two pieces of a thermoplastic resin such as nylon, styrene-acrylic copolymer, polystyrene, or polycarbonate using known micro-injection molding processes. The mold for making the obstructions in the capillary pathway can be constructed by deep reactive ion etching processes typically employed in the manufacture of molds for pre-recorded compact disks and digital video disks. A reaction region is generally also formed by the same process at an outlet end of the capillary pathway which is generally vented to ensure that there is no opposition to the fast capillary flow of liquid through the capillary pathway. The capillary pathway and the reaction region in the molded structure is then preferably subjected to a hydrophilizing process such as by plasma etching or DONS solution. A suitable dry reagent can be situated in the reaction region, if desired. The pieces of the structure are then assembled so that the capillary pathway and reaction region are enclosed within the structure, yet can be accessed at an inlet port designed to receive a sample of blood.

The resulting structure can be viewed as an apparatus for separating hematocrit from a whole blood sample having a selected total volume, the sample including a partial volume of blood plasma and a partial volume of hematocrit. The fundamental features of the apparatus comprise a body having an inlet port for receiving a whole blood sample, a vented reaction region spaced from the inlet port, and at least one capillary pathway having an inlet end coupled to the inlet port and an outlet end coupled to the vented reaction region, each capillary pathway being dimensioned sufficiently small to assure transport of blood plasma from the inlet end to the outlet end by capillary pressure delivering a reaction volume of plasma to the reaction region, each capillary pathway including a plurality of obstructions, each of the obstructions having a concave portion facing toward the outlet end of the pathway, the sum of the concave portions having sufficient volume to contain at least an appreciable fraction of the hematocrit partial volume. Preferably, the total volume of the concave portions of all of the obstructions is at least equal to the reaction volume times the ratio of the partial volume of the hematocrit to the total volume of the sample. Generally, the capillary pathway volume is less than the sum of the partial volumes of the blood plasma and hematocrit.

Other advantageous features will become apparent upon consideration of the following description of preferred embodiments which references the attached drawings.

DESCRIPTION OF PREFERRED EMBODIMENTS

Figure 1:
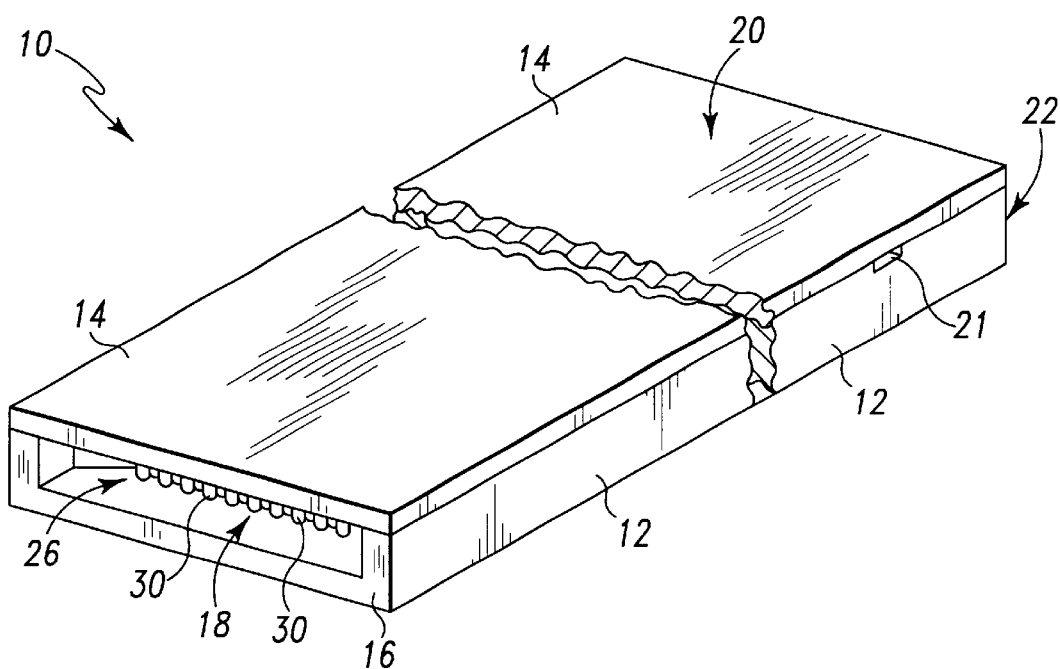
FIG. 1 is a perspective view of a capillary hematocrit separation structure according to the present invention.
Figure 2:
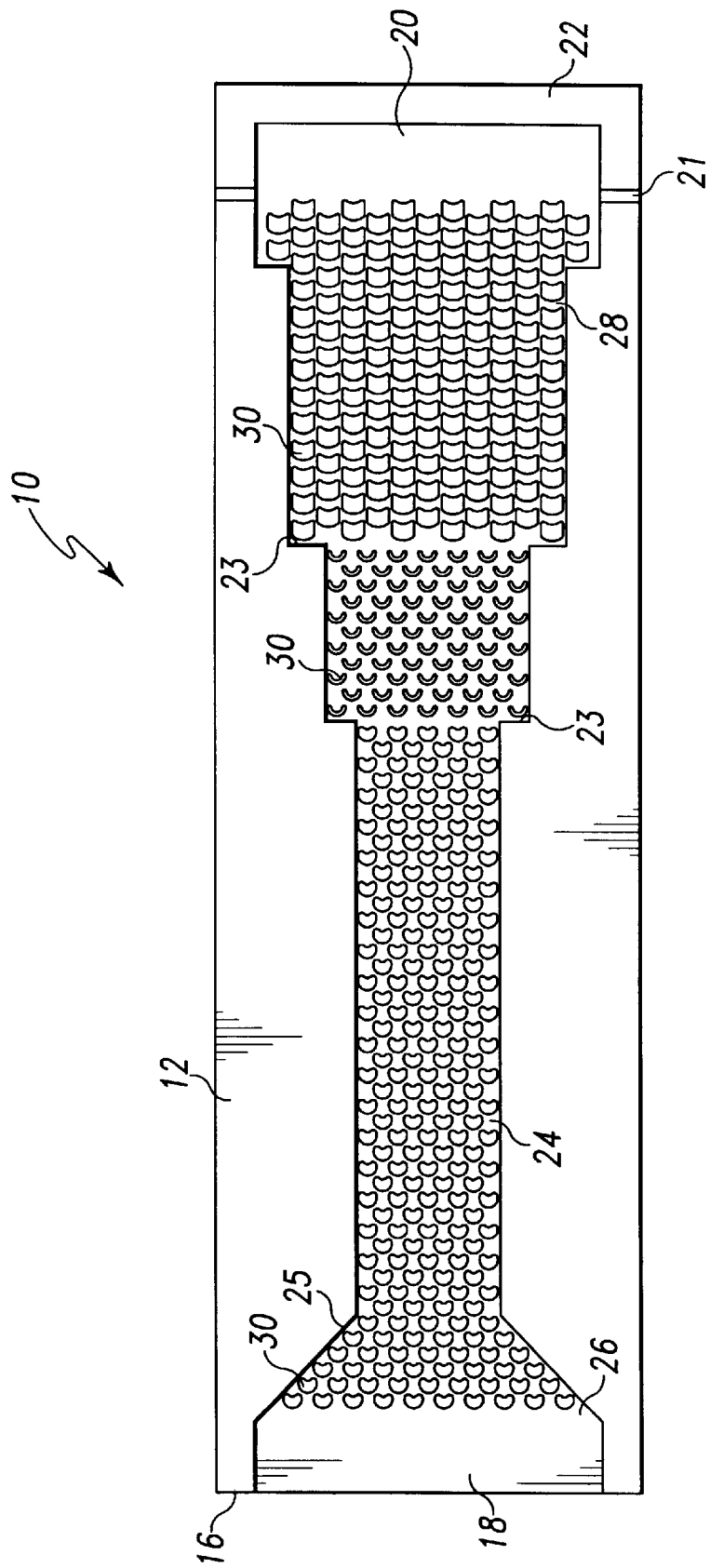
FIG. 2 is a plan view of the capillary hematocrit separation structure shown in FIG. 1 with the cover removed.

An apparatus 10 for separating hematocrit from a whole blood sample according to the present invention is shown in FIGS. 1 and 2. The apparatus includes a body 12 and a cover 14. A first end 16 includes an inlet port 18 for receiving a whole blood sample. A reaction region 20, generally including a vent 21, is spaced from the inlet port 18 and can be situated adjacent a second end 22. At least one capillary pathway 24 has an inlet end 26 coupled to the inlet port 18 and an outlet end 28 coupled to the reaction region 20. The capillary pathway 24 is dimensioned sufficiently small to assure transport of blood plasma from the inlet end 26 to the outlet end 28 by capillary pressure to deliver a reaction volume of plasma to the reaction region 20. The capillary pathway 24 includes a plurality of obstructions 30, the obstructions 30 having a concave portion 32 facing toward the outlet end 28 of the capillary pathway 24. Preferably, the total volume of the concave portions 32 of all of the obstructions 30 is at least equal to the volume of the reaction region 20 times the ratio of the partial volume of the hematocrit to the total volume of a typical sample likely to be applied to the apparatus 10. Generally, the volume of the capillary pathway 24 is less than the sum of the partial volumes of the blood plasma and hematocrit in a typical sample likely to be applied to the apparatus 10.

Figure 3:
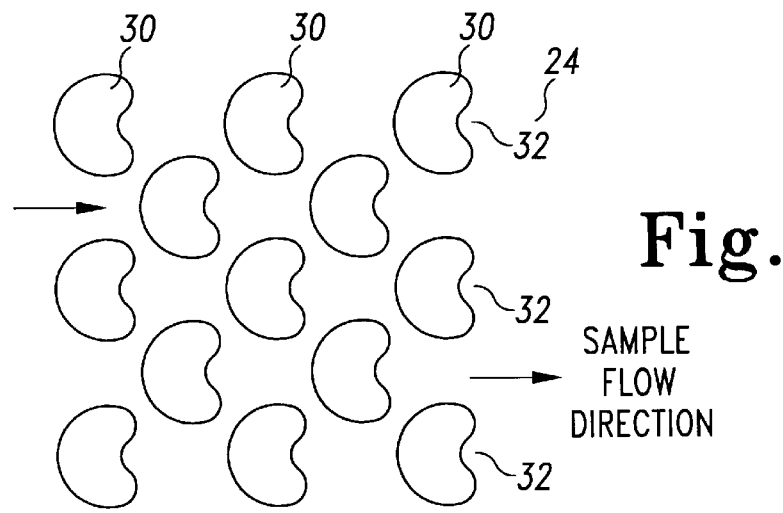
FIG. 3 is a detail view of a portion of the capillary pathway in the capillary hematocrit separation structure shown in FIG. 1 showing a first preferred embodiment for the obstructions.
Figure 4:
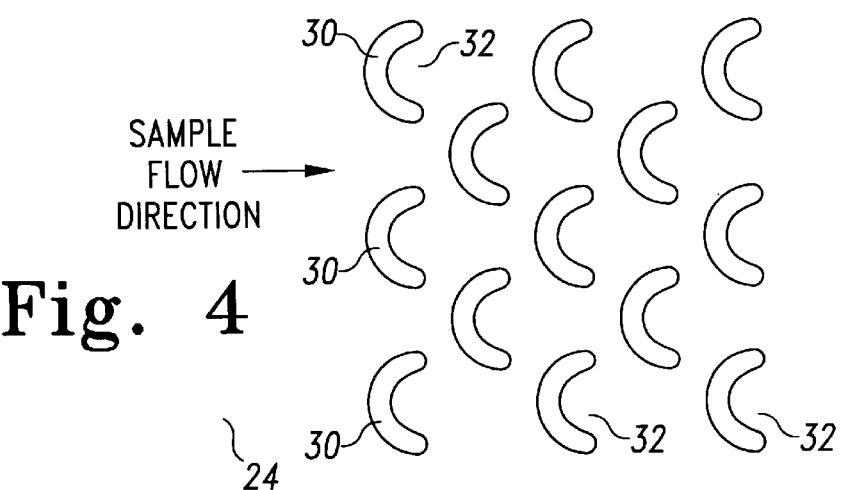
FIG. 4 is another detail view of a portion of the capillary pathway showing an alternative embodiment for the obstructions.
Figure 5:
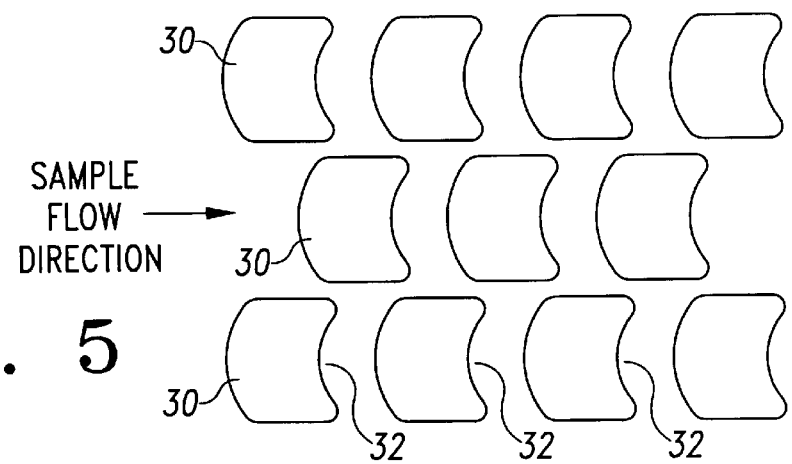
FIG. 5 is yet another detail view of a portion of the capillary pathway showing another alternative embodiment for the obstructions.

Three possible shapes for the obstructions 30 are shown in FIGS. 3–5 in relation to the direction of liquid flow through the capillary pathway 24.

FIGS. 3–5 are not intended to exhaust all possible shapes for the obstructions 30, but merely illustrate shapes having utility in the present invention. In all three shapes the obstructions 30 are illustrated to include a concave portion 32, outlined in phantom, facing down stream with respect to the direction of liquid flow. The size of the concave portion 32 should probably be evaluated in relation to the total liquid-containing volume between the obstructions 30 rather than in relation to the size of the obstructions. While, the size of the obstructions 30 is believed to play some role in the performance of the apparatus 10, a greater role is believed to be played by the proportion of concave volume to total liquid-containing volume, which is related to the spacing and arrangement of the obstructions 30 within the capillary pathway 24 as well as the size of the concave portions 32. The shape of the concave portion 32 need not include a smooth curve as illustrated in FIGS. 3–5, and instead can be angular such as triangular or rectangular.

The capillary pathway 24 in such a structure 12 can be a rectangular channel about 100 μm high or less, 2 to 5 mm wide, and up to 70 mm long. The channel height and width does not have to be constant throughout the whole length, and can include steps 23 and/or ramps 25 that transition from one channel height or width to another as shown generally in FIG. 2. Each obstruction 30 preferably extends over the entire height of the pathway 24. It will be appreciated that, in principle, such obstructions should also operate if oriented horizontally rather than vertically in the pathway 24, as illustrated, but that the manufacture of an array of such horizontal obstructions might be difficult. In the preferred embodiment, the obstructions 30 are vertically oriented and have a diameter of about 50 μm in the width dimension of the channel. The obstructions 30 are preferably separated from their nearest neighbor by a distance of about 10 μm.

Figure 6A:
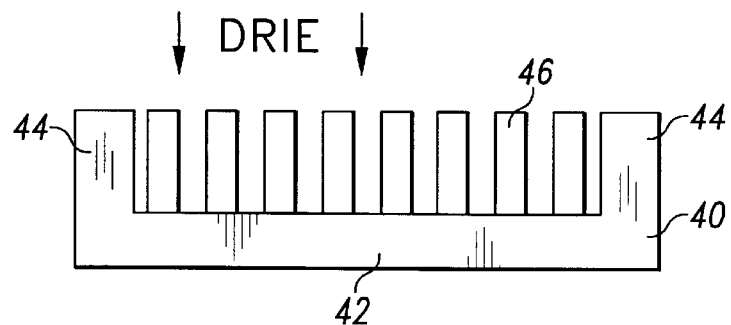
FIGS. 6A–6E schematically illustrate the preferred method for creating the capillary hematocrit separation structures of the present invention.
Figure 6B:
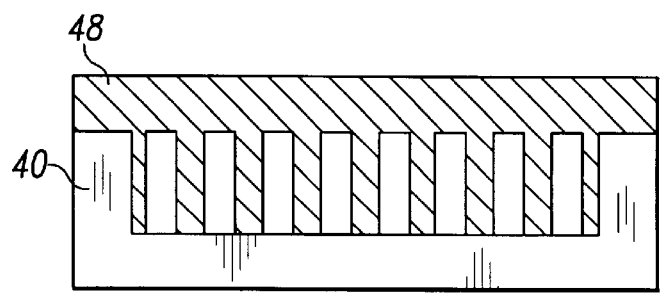
Figure 6C:
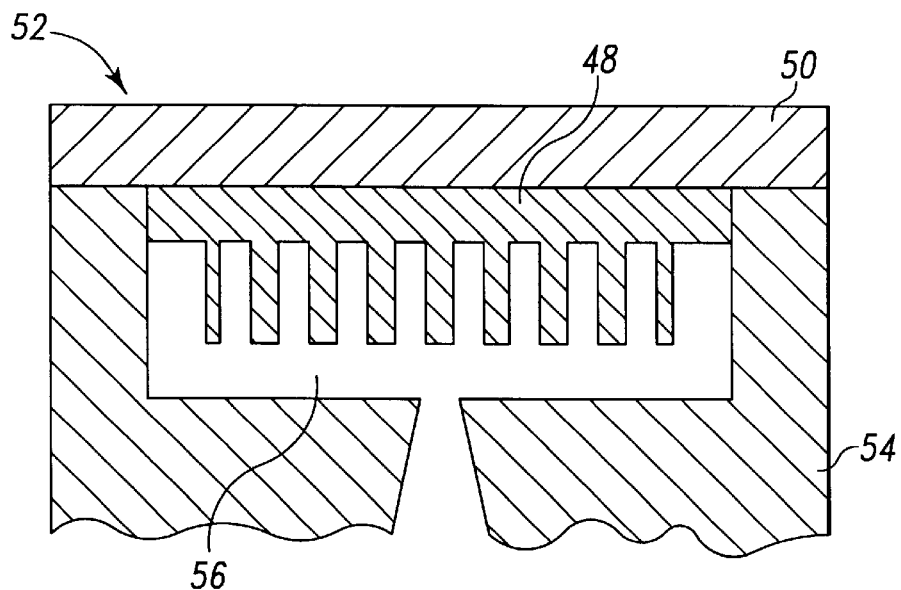
Figure 6D:
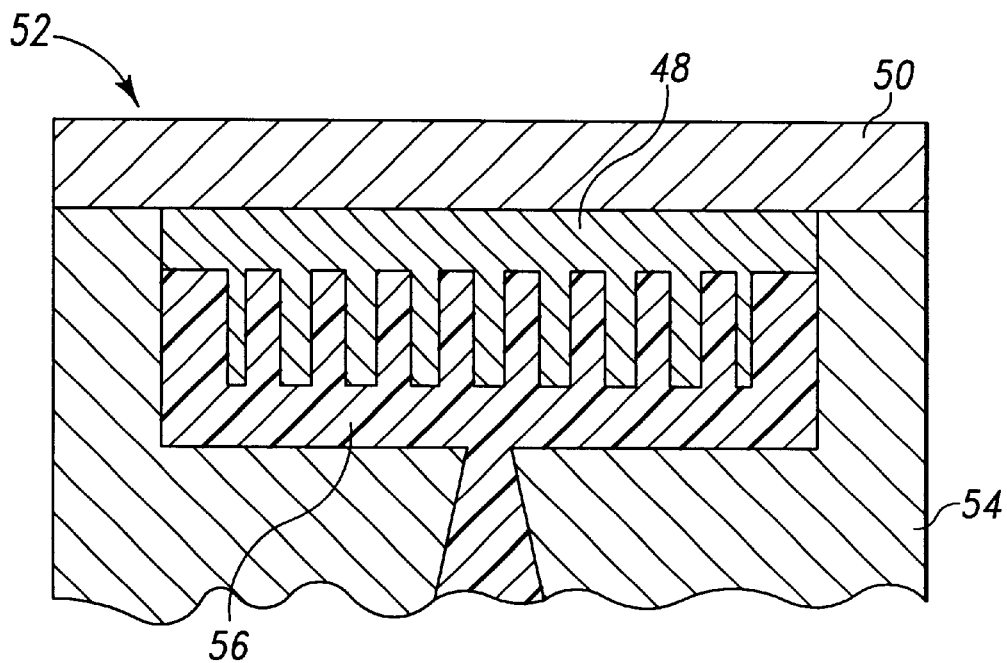
Figure 6E:
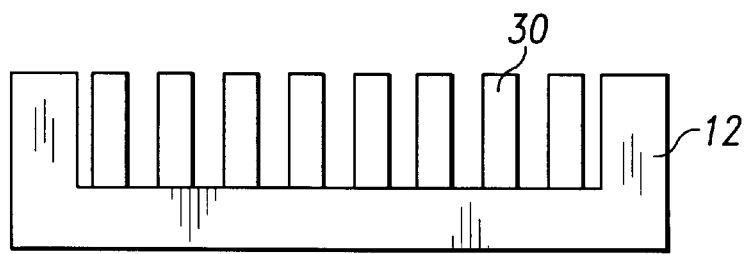

The hematocrit separation structures of the present invention can be molded of plastic using micro-injection technology similar to that employed in pre-recorded CDs and DVDs. The process is outlined in FIGS. 6A through 6E. First, a master tool 40 is produced in silicon by using a deep reactive ion etching process. The master tool 40 is shown in FIG. 6A to include the floor 42 and the side walls 44 of the channel defining the capillary pathway 24. The floor 42 in the master tool 40 includes the master structures 46 that reflect the obstructions 30 of the present invention. The master tool 40 is then employed to create in FIG. 6B one or more working negative tools 48, generally constructed of nickel, that can be employed in the subsequent steps of the manufacturing process. A working negative tool 48 is then mounted to a mold tool support fixture 50 as shown in FIG. 6C. The negative tool 48 and support fixture 50 form a one portion 52 of a mold pair, the other portion 54 being constructed using standard EDM or other machining techniques. The two mold portion 52 and 54 can then be operated in an micro-injection molding machine to define a cavity 56 for receiving plastic resin, such as a polycarbonate, to form an apparatus 10 in accordance with the present invention. Generally, the body 12 and cover 14 will be formed at the same time in the same process in adjacent mold sections to facilitate assembly of the apparatus 10.

Prior to assembly, the body 12 and cover 14 will usually be subjected to a suitable hydrophilizing process covering at least the capillary pathway 24 and reaction region 20. The selection of the particular process is generally suggested by, if not dictated by, the resin employed to manufacture the apparatus 10. The process can be physical, such as plasma etching, or chemical, such as an application of DONS solution. Following the hydrophilizing process, a desired reagent can be added into the reaction region 20. The cover 14 is then fixed in place to the body 12 by suitable means such as by mechanical coupling or by solvent or ultrasonic bonding.

In use, the apparatus 10 can be employed as a clinical diagnostic device to detect an analyte such as blood sugar level in blood plasma. Usually, a suitable, generally dry reagent is provided in the reaction region 20 to interact with any plasma that passes through the capillary pathway 24. A whole blood specimen is applied to the inlet port 18 and the specimen is pulled down the length of the capillary pathway 24 by capillary pressure. As the specimen proceeds through the capillary pathway 24, it encounters the plurality of obstruction 30, each obstruction having a concave portion 32 on the back side or down stream side. As the specimen proceeds through the capillary pathway 24, hematocrit is observed to collect in the concave portions 32 in an amount exceed the average concentration in the specimen. As a result, the concentration of hematocrit in the specimen diminishes as it proceeds through the capillary pathway toward the reaction region 20. As the blood plasma containing a reduced concentration of hematocrit arrives at the reaction region, the plasma wets and reacts with the reagent. The reaction can be observed through the body 1 2 or the cover 14 with at least a reduced interference from any hematocrit still remaining in the sample. The observations can be made optically, electrically, or by other means suitable to quantitatively evaluate the reaction results. For example, the reaction region 20 can include an optical window permitting optical detection of an analyte in the blood plasma. Alternatively or in addition, the reaction region 20 can include electrochemical apparatus for detection of an analyte in the blood plasma.

Although the present invention has been described by reference to the illustrated preferred embodiment, it will be appreciated by those skilled in the art that certain changes and modifications can be made within the scope of the invention as defined by the appended claims.

What is claimed is:

1. An apparatus for separating hematocrit from a whole blood sample having a selected total volume, the sample including a partial volume of blood plasma and a partial volume of hematocrit, the apparatus comprising:
    a body having an inlet port for receiving a whole blood sample, a reaction region spaced from the inlet port, and at least one capillary pathway having an inlet end coupled to the inlet port and an outlet end coupled to the reaction region, each capillary pathway being dimensioned sufficiently small to assure transport of a portion of the blood sample from the inlet end to the outlet end by capillary pressure, each capillary pathway including a plurality of obstructions, the obstructions having a concave portion facing toward the outlet end of the pathway for separating hematocrit from the portion of the blood sample transported through the capillary pathway to deliver a reaction volume of plasma to the reaction region.

2. The apparatus of claim 1 wherein the concave portions of all the obstructions have a total volume at least equal to the reaction volume times the ratio of said partial volume of the hematocrit to said total volume of the sample.

3. The apparatus of claim 1 wherein each capillary pathway volume is less than the sum of said partial volumes of the blood plasma and hematocrit.

4. The apparatus of claim 1 wherein the obstructions, in cross-section, have a crescent moon shape.

5. The apparatus of claim 1 wherein the obstructions, in cross section, have a bullet shape.

6. The apparatus of claim 1 wherein the obstructions are separated from each other, on a nearest neighbor basis, by about $10^{-5}$ meters.

7. The apparatus of claim 1 wherein the inlet port has a volume that is less than about 50 $\mu$l.

8. The apparatus of claim 7 wherein the sum of the inlet port volume and the capillary pathway volume is less than about 20 $\mu$l.

9. The apparatus of claim 1 wherein the reaction region contains a dry reagent selected to detect an analyte in the blood plasma.

10. The apparatus of claim 1 wherein the reaction region includes an optical window permitting optical detection of an analyte in the blood plasma.

11. The apparatus of claim 1 wherein the reaction region includes electrochemical apparatus for detection of an analyte in the blood plasma.

12. In a clinical diagnostic device comprising a housing having a fluid inlet port, a vented reaction region, and at least one capillary pathway connecting the inlet port and the reaction region and in which the driving force for the movement of liquid through the at least one capillary pathway arises from capillary pressure, an improvement comprising:
    a plurality of obstructions fixed in the at least one capillary pathway, each obstruction having a concave portion facing toward the vented reaction region.

13. The clinical diagnostic device of claim 12 wherein the obstructions, in cross-section, have a crescent moon shape.

14. The clinical diagnostic device of claim 12 wherein the obstructions, in cross-section, have a bullet shape.

15. The clinical diagnostic device of any of claims 12–14 wherein the obstructions are separated from each other, on a nearest neighbor basis, by about $10^{-5}$ meters.

16. The clinical diagnostic device of claim 15 wherein the inlet port has a volume that is less than about 50 $\mu$l.

17. The clinical diagnostic device of claim 16 wherein a sum of the inlet port volume and the volume of the at least one capillary pathway is less than about 20 $\mu$l.

18. The clinical diagnostic device of claim 15 wherein the reaction region contains a dry reagent selected to detect an analyte in a liquid applied to the device.

19. The clinical diagnostic device of claim 15 wherein the reaction region includes an optical window permitting optical detection of an analyte in a liquid applied to the device.

20. The clinical diagnostic device of claim 15 wherein the reaction region includes electrochemical apparatus for detection of an analyte in a liquid applied to the device.

21. The clinical diagnostic device of any of claims 12–14 wherein the inlet port has a volume that is less than about 50 $\mu$l.

22. The clinical diagnostic device of any of claims 12–14 wherein a sum of the volume of the inlet port and the at least one capillary pathway is less than about 20 $\mu$l.

23. The clinical diagnostic device of any of claims 12–14 wherein the reaction region contains a dry reagent selected to detect an analyte in a liquid applied to the device.

24. The clinical diagnostic device of any of claims 12–14 wherein the reaction region includes an optical window permitting optical detection of an analyte in a liquid applied to the device.

25. The clinical diagnostic device of any of claims 12–14 wherein the reaction region includes electrochemical apparatus for detection of an analyte in a liquid applied to the device.

26. A method for detecting an analyte in blood plasma comprising the steps of:

provtding a reagent in a reaction region of a clinical diagnostic device, separating a specimen amount of blood plasma from a whole blood sample by:

introducing a whole blood sample containing a partial volume of blood plasma into an inlet end of a capillary pathway leading to the reaction region, the capillary pathway containing a plurality of obstructions fixed in the capillary pathway, each obstruction having a concave portion facing away from the inlet end in the direction of flow of the blood sample from the inlet end to the reaction region, allowing sufficient time for the specimen amount of blood plasma to flow through the length of the capillary pathway to the reaction region, and observing the reaction between the blood plasma and the reagent in the reaction region of the device to detect said analyte.

27. The method of claim 26 further comprising the step of hydrophilizing the capillary pathway and reaction region prior to the introducing step.

* * * * *